(12) United States Patent
Andrews et al.

(10) Patent No.: US 6,673,421 B1
(45) Date of Patent: Jan. 6, 2004

(54) STOCKING HAVING A SEAMLESSLY ATTACHED ANTISLIP COATING IN THE EDGE REGION OF THE UPPER OPENING

(75) Inventors: Arthur-Hugh Andrews, Kölln-Reisiek (DE); Stefan Bodenschatz, Buxtehude (DE); Peter Himmelsbach, Buxtehude (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/644,302

(22) Filed: Aug. 23, 2000

(30) Foreign Application Priority Data

Aug. 24, 1999 (DE) ......................... 199 40 018

(51) Int. Cl.⁷ ............................... B32B 27/12
(52) U.S. Cl. ................. 428/193; 428/197; 442/101; 2/239
(58) Field of Search .............. 442/101; 2/239; 428/193, 197

(56) References Cited

U.S. PATENT DOCUMENTS

| 2,514,108 A | 7/1950 | Vogt ............ 2/240 |
| 3,983,870 A | * 10/1976 | Herbert et al. |

FOREIGN PATENT DOCUMENTS

| DE | 1 610 580 | 11/1966 | ........ A41B/11/00 |
| DE | 27 16 306 C2 | 11/1977 | ........ A61F/13/08 |
| DE | 88 14047 U1 | 2/1989 | ........ A61F/13/08 |
| DE | 39 02 434 A1 | 8/1990 | ........ A61L/15/00 |
| DE | 39 16 040 C2 | 10/1990 | ........ A41H/43/00 |
| DE | 196 20 109 A1 | 11/1997 | ........ C09J/7/04 |
| DE | 198 24 649 A1 | 11/1999 | ........ A61F/13/00 |
| EP | 0 516 994 A1 | 12/1992 | ........ D06N/3/14 |
| WO | 95/12370 A1 | 5/1995 | ........ A61F/13/00 |

OTHER PUBLICATIONS

Römpp Lexikon Chemie—Ver. 2.0, Stuttgart/New York:Georg Thieme Verlag 1999.

* cited by examiner

Primary Examiner—Elizabeth M. Cole
(74) Attorney, Agent, or Firm—Norris McLaughlin & Marcus, P.A.

(57) ABSTRACT

Stocking having a seamlessly attached antislip coating in the edge region of the upper opening of the stocking, the edge of the stocking producing a compressive pressure of from 3 to 45 mm Hg at an extension of from 10% to 350% and having a width-based flexural stiffness (DIN 53121) of at least 20 cN×mm and, in the region of the stocking opening, the bond strength of the coating to the stocking being at least 3 N/cm.

26 Claims, 1 Drawing Sheet

STOCKING HAVING A SEAMLESSLY ATTACHED ANTISLIP COATING IN THE EDGE REGION OF THE UPPER OPENING

The invention relates to a stocking having a seamlessly attached antislip or nonslip coating in the edge region of the upper opening of the stocking, especially an antithrombosis stocking.

Medical stockings are known. Owing to their compressive properties, they improve the rate of flow through the veins. For immobilized patients, stockings are used prophylactically to prevent embolisms or thromboses.

Antislip or nonslip treatments for such stockings are likewise known. In particular, antislip coatings are described for the sole region or the edge region at the opening of the stocking.

In the prior art, these coatings are based on natural and synthetic polymers. In particular, the use of amide, silicone, acrylate, vinyl and styrene compounds, and of rubber and latex as well, is known.

A first disadvantage of these compounds is the low washing resistance at relatively high temperatures or the limited adhesion to the stocking. Secondly, chemically reactive compounds are difficult to prepare or are objectionable in terms of their compatibility, especially in contact with the skin. Furthermore, wash-resistant coatings are hard and fairly unconforming.

Current products on the stockings market include an antislip edge at the upper opening of the stocking, which has been applied separately, often by sewing.

This is disadvantageous not only in terms of costs but also as regards handling in the manufacturing process. Advantages, however, include the flexibility in product design, and the strength of the combined unit. Moreover, this edge, which generally comprises a different material, protects the stocking edge against turning over.

U.S. Pat. No. 3,983,870 discloses a slip-resistant support for limbs, especially a medical stocking. The nonslip coating is produced using, inter alia, acrylates and rubbers. In a further listing of substances, without any indication of a possible teaching, undifferentiated mention is made of thermosetting urethanes, whereas crosslinked oligomeric diols are not disclosed.

A sewn-on grip edge is described in the disclosure.

DE 25 05 923 shows a stocking for medical applications, the antislip strip present on the stocking having been fastened with a Merrow seam.

U.S. Pat. No. 5,412,957 discloses an antislip feature in the sole area of the medical stocking. The required flexural stiffness is not described.

FR 2 609 889 describes a special pattern for an antislip ribbon. There is no description of seamless attachment of an antislip ribbon.

DE 39 16 040 describes a method of applying antislip compositions to articles of clothing, in which the articles of clothing are turned inside out. Subsequently, they are caused to rotate about their longitudinal axis. In this case, reactive silicone rubbers, in particular, are used to form the antislip compositions. Owing to the reactivity the process is very complex, since silicones require curing.

U.S. Pat. No. 3,728,875 describes a stocking having a soft inner portion, where an elastic tape based on urethane is sewn on. The teaching does not disclose whether the compounds in question are crosslinked oligomeric diols. Moreover, the attachment of such a tape is expensive, making it disadvantageous as compared with simple treatment by coating. Likewise, a high flexural stiffness is not described.

WO 97/45081 discloses a stocking for medical purposes, having a special polyurethane thread for generating compression. In addition, a strip is attached on the ankle region. Not shown, in contrast, is the seamless attachment of the strip.

The object of the invention is to provide a stocking which features an antislip coating, is suitable for medical requirements, and does not have the disadvantages known from the prior art.

This object is achieved by means of a stocking as specified in the main claim. The subsidiary claims embrace advantageous variants of the subject-matter of the invention.

The invention accordingly provides a stocking having a seamlessly attached antislip or nonslip coating in the edge region of the upper opening of the stocking, the edge of the stocking producing a compressive pressure of from 3 to 45 mm Hg at an extension of from 10% to 350% and having a width-based flexural stiffness (DIN 53121) of at least 20 cN×mm. Furthermore, in the region of the stocking opening, the bond strength of the coating to the stocking is at least 3 N/cm.

The coating preferably comprises a polyadduct having a phase 1 and a phase 2, the mass fraction of phase 1 being greater than 60% by weight.

Phase 1 is a polyadduct of at least one starting material E1 and at least one starting material E3, starting material E1 comprising an oligomeric diol which has a hydroxyl number of more than 20 mg KOH/g (diol) and starting material E3 comprising a silicone-free, at least bifunctional reactive starting material having a molecular weight of less than 300 g/mol.

Phase 2 is a polyadduct comprising at least one starting material E2 and at least one starting material E3, the starting material E2 having, at least in part, terminal functional groups.

The coating features a molar ratio between the starting materials E3 to be crosslinked and the sum of one or more oligomeric diols (starting material E1) and the fraction of further starting materials E2 of from 0.9 to 1.1.

According to Römpp (Römpp Lexikon Chemie—Version 1.5, Stuttgart/New York: Georg Thieme Verlag 1998) the hydroxyl number describes an index which indicates how many milligrams of potassium hydroxide are equivalent to the amount of acetic acid bound by 1 g of substance in the course of acetylation. The sample is generally boiled with acetic anhydride-pyridine and the acid formed is titrated with KOH solution. The hydroxyl number, which is used to assess reactive resins, waxes, fats, oils, solvents, etc., is related—in Anglo-American investigations, identical—to the acetyl number. Further details may be found in the DIN Standards 53 240 (12/1971) and 53 240-2 (12/1993).

In one preferred embodiment, the ratio of the mass fraction of phase 1 and phase 2 is greater than 1.5. In other advantageous embodiments it is between 1.8 and 100, with particular advantage from 2.0 to 20. More preferably, the mass fraction of phase 1 is between 67% by weight and 98% by weight. Particularly advantageous polyadducts have a weight fraction of from 75% by weight to 95% by weight in phase 1, with particular suitability from 76% by weight to 95% by weight.

A modified functional antislip coating is achieved by the foaming thereof.

The antislip substances to be used are in this case foamed preferably using inert gases such as nitrogen, carbon dioxide, noble gases, hydrocarbons or air, or mixtures thereof. In many cases, foaming additionally by the thermal decomposition of gas-evolving substances such as azo, carbonate and hydrazide compounds has proved to be suitable.

The degree of foaming, i.e. the gas fraction, should be at least approximately 5% by volume and may extend up to approximately 85% by volume. In practice, values of from 10% by volume to 75% by volume, preferably from 20 to 60% by volume, with particular preference from 40 to 60% by volume, have been found to be good. If foaming is carried out at relatively high temperatures of from approximately 100° C. to 240° C. with a comparatively high internal pressure, it is possible for very open-pored antislip foam layers to be obtained, which are particularly permeable to air and water vapour. The advantageous properties of the foamed coating are its good conformity even to uneven surfaces, by virtue of the elasticity and plasticity of the foamed device.

A particularly suitable process for preparing the antislip coating foamed in accordance with the invention operates in accordance with the foam mix system. Here, the thermoplastic antislip composition is reacted under high pressure at a temperature above the softening point (approximately 180° C.) with the intended gases such as, for example, nitrogen, air or carbon dioxide in different volume proportions (from about 10% by volume to 80% by volume) in a stator/rotor system.

While the gas entry pressure is greater than 100 bar, the gas/thermoplastic mixed pressures within the system are from 40 to 100 bar, preferably from 40 to 70 bar. The antislip foam produced in this way may subsequently pass through a line into the applicator unit. As regards the applicator unit, commercially customary nozzle, extruder or chamber systems are used.

By virtue of the foaming of the coating and the resultant open pores in the composition, and when using a stocking material which is inherently porous, the stocking regions coated with the antislip coating feature good permeability to water vapour and air. The amount of antislip composition needed is considerably reduced without adversely affecting the mode of action or properties.

It is further advantageous if the composition is applied partially to the edge region of the stocking, for example by halftone printing, thermal screen printing, thermal flexographic printing or gravure printing, since backing materials coated in solid lines may, under adverse circumstances, give rise to instances of mechanical skin irritation in the course of the application.

Furthermore, the antislip coating may also, for example, be sprayed on or spun, producing a more or less irregular application pattern.

The partial application makes it possible for the transepidermal water loss to be dissipated through regulated channels, and improves the evaporation of perspiration from the skin, especially when the stocking materials used are permeable to air and water vapour. This prevents instances of skin irritation induced by build-up of body fluids. The dissipation channels employed permit such fluids to be conducted away.

Preference is given to application in the form of polygeometric domes, and very particularly domes where the ratio of diameter to height is less than 5:1. Also possible is the printing of other shapes and patterns onto the stocking material; for example, a printed image in the form of combinations of alphanumeric characters or patterns such as grids, stripes and zigzag lines.

The antislip substance may be distributed uniformly over the stocking material; alternatively, it may be applied in different thicknesses or concentrations over the area in a manner appropriate to the function of the product.

The principle of thermal screen printing consists in the use of a rotating, heated, seamless, drum-shaped, perforated, cylindrical screen which is fed via a nozzle with the preferred composition. A specially shaped nozzle lip (circular or square-section coating bar) presses the composition, which is fed in via a channel, through the perforation of the screen wall and onto the backing web that is conveyed past it. This backing web is guided by means of a counter pressure roller against the external jacket of the heated screen drum at a rate which corresponds to the peripheral speed of the rotating screen drum.

In the course of this process, the small domes are formed in accordance with the following mechanism:

The pressure of the nozzle coating bar conveys the composition through the screen perforation onto the backing material. The size of the domes that have formed is dictated by the diameter of the screen perforation. The screen is lifted from the backing in accordance with the rate of transportation of the backing web (rotary speed of the screen drum). As a consequence of the adhesion of the antislip composition in the melt and of the internal cohesion of the hot-melt, the limited supply of antislip substance in the perforations is drawn in sharp definition from the base of the domes, which is already adhering to the backing, and is conveyed onto the backing by the pressure of the coating bar.

Following the end of this transportation, the more or less highly curved surface of the dome forms over the predefined base area in dependence on the rheology of the antislip composition. The height-to-base ratio of the dome depends on the ratio of the perforation diameter to the wall thickness of the screen drum and on the physical properties (rheology, surface tension and contact angle on the backing material) of the composition.

For the screen in thermal screen printing, the web-to-hole ratio can be less than 10:1, preferably less than or equal to 1:1, in particular equal to 1:10.

The above-described mechanism of formation of the domes requires, preferentially, stocking materials that are absorbent or are at least wettable by the cohesive composition.

Stocking surfaces that are difficult to wet must be pretreated by chemical or physical methods. This can be done by means of additional measures, such as, for example, corona discharge or coating with substances which improve wetting.

Using the printing technique indicated, it is possible to lay down the size and shape of the domes in a defined manner. The chosen base diameter of the domes may be from 10 $\mu$m to 10,000 $\mu$m, the height of the domes from 20 $\mu$m to 2000 $\mu$m, preferably from 50 $\mu$m to 1000 $\mu$m, the small-diameter range being envisaged for smooth stockings while the range comprising greater diameter and greater dome height is envisaged for rough or highly porous stocking materials.

The positioning of the domes on the stocking is laid down in a defined manner by the geometry of the applicator unit, for example the gravure or screen geometry, which can be varied within wide limits. With the aid of the parameters indicated it is possible, by way of adjustable variables, to establish with very great precision the desired profile of properties of the coating, tailored to the various backing materials and applications.

The stocking material is preferably coated at a rate of greater than 2 m/min, preferably from 20 to 220 m/min, the coating temperature chosen being greater than the softening temperature.

The antislip or nonslip composition may be applied to the stocking material with a weight per unit area of greater than 3 g/m², preferably between 6 g/m² and 1000 g/m², with very particular preference between 9 g/m² and 750 g/m². For one specific stocking coating, weights per unit area of from 300 to 700 g/m² are necessary. In this case, small cutouts are utilized for the stocking edge with a high width-based flexural stiffness (DIN 53121).

The percentage area that is partially coated with the composition should be at least 5% and may be up to approximately 95%, for specific products preferably from 20% to 60% and from 70% to 95%. This may be achieved, if desired, by means of multiple application or special deformation steps, it being possible, if desired, to use compositions having different properties as well. In the case of special stocking applications, from 10 to 50% of the coating region is coated.

Antislip coatings used are substances on a thermoplastic basis which feature good washability, skin compatibility and thermal stability.

Advantageous substances are those which suffer little or no mass shrinkage as a result of washing with conventional laundry detergents. The substances used, at least at a wash temperature in the range from 5 to 96° C. or at temperatures around and above 100° C., exhibit a mass shrinkage of less than 10% after at least five wash cycles. The antislip coating should therefore be stable to hydrolysis especially within the temperature range from 5° C. to 100° C.

For a conforming, antislip or nonslip coating it is advantageous to use at least partly linear polymers based on crosslinked oligomeric diols (E1), because uncrosslinked oligomeric diols possess little or no stability to washing. Moreover, no antislip or nonslip effect can be found in the case of uncrosslinked diols.

The oligomeric diol for use is generally a product of synthesis which is reacted by poly-addition to give an antislip material. For specific use as an antislip or nonslip substance, oligomeric diols having a hydroxyl number (DIN 53240) of at least 20 are needed, preferably from 40 to 230 mg KOH/g, with particular preference from 65 to 224 mg KOH/g, with very particular preference from 70 to 150 mg KOH/g. When selecting the diols, care should be taken to ensure sufficient hydrolytic stability. Polyethers, special polyesters, polyacrylic and methacrylic acid compounds can be used. In general, polyethers based on polyethylene oxide diol, polypropylene oxide diol and polytetramethylene oxide diol are advantageous.

Representatives of the second starting-material group (E2) are low molecular mass diols or diamines. Mention may be made here of ethanediol, butanediol and hexanediol, and also various aliphatic diamines. In each case terminal attachment of the hydroxyl or amino group is likewise advantageous. The starting material E2 is preferably a 1,2-ethanediol, 1,4-butanediol, 1,6-hexanediol and/or a mixture of the aforementioned materials.

Representatives of the third starting-material group (E3) likewise have, at least in part, terminal functional groups. Particular preference for crosslinking is given to the use of one or more silicone-free bifunctional reactive starting materials having a molecular weight of less than 300 g/mol in the initial form. The most important representatives of this group are compounds containing epoxide and isocyanate. Preferably, the starting material E3 is an aliphatic or aromatic diisocyanate.

In one preferred embodiment, the coating comprises less than 5% by weight of allophanate groups, preferably from 0.01 to 2% by weight.

Then it is advantageous for the antislip coating if the coating is hydrolytically stable within the temperature range from 5° C. to 100° C.

Depending on the use, substances with an initiator, catalyst or stabilizer effect may be added to the antislip coating.

In order to obtain an additional effect, active substances may also be added to the coating, preferably in quantitative concentrations of the active substance or substances of from 0.01 to 50% by weight, preferably from 0.1 to 20% by weight.

By "active substances" in connection with the present invention are meant chemical elements, organic and inorganic compounds which are able to migrate from the constituents of a generic coating that comprise them and so bring about a desired effect. Among the fields of use of the coating of the invention, human and veterinary medicine are of particular importance.

Typical substances that may be administered in this case are the following:

aceclidine, amfetaminil, amfetamine, amyl nitrite, apophedrine, atabrine, alprostadil, azulene, arecoline, anethole, amylene hydrate, acetylcholine, acridine, adenosine triphosphoric acid, L-malic acid, alimemazine, allithiamine, allyl isothiocyanate, aminoethanol, apyzine, apiole, azatadine, alprenolol, ethinazone, benzoyl peroxide, benzyl alcohol, bisabolol, bisnorephedrine, butacetoluide, benactyzine, camphor, colecalciferol, chloral hydrate, clemastine, chlorobutanol, capsaicin, cyclopentamine, clobutinol, chamazulene, dimethocaine, codeine, chlorpromazine, quinine, chlorothymol, cyclophosphamide, cinchocaine, chlorambucil, chlorphenesin, diethylethane, divinylethane, dexchlopheniramine, dinoprostone, dixyrazine, ephedrine, ethosuximide, enallylpropymal, emylcamate, erythrol tetranitrate, emetine, enflurane, eucalyptol, etofenamate, ethylmorphine, fentanyl, fluanisone, guaiazulene, halothane, hyoscyamine, histamine, fencarbamide, hydroxycaine, hexylresorcinol, isoaminile citrate, isosorbide dinitrate, ibuprofen, iodine, iodoform, isoaminile, lidocaine, lopirine, levamisole, methadone, methyprylon, methylphenidate, mephenesin, methylephedrine, meclastine, methopromazine, mesuximide, nikethamide, norpseudoephedrine, menthol, methoxyfluran, methylpentinol, metixene, mesoprostol, oxytetracaine, oxyprenolol, oxyphenbutazone, oxyquinoline, pinene, prolintane, procyclidine, piperazine, pivazide, phensuximide, procaine, phenindamine, promethazine, pentetrazole, profenamine, perazine, phenol, pethidine, pilocarpine, prenylamine, phenoxybenzamine, Resochin, scopolamine, salicylic acid ester, sparteine, trichloroethylene, timolol, trifluoperazine, tetracaine, trimipramine, tranylcypromine, trimethadione, tybamate, thymol, thioridazine, valproic acid and verapamil, and also other active substances familiar to the skilled worker that can be absorbed through the skin. This list is of course not exhaustive.

The dispersal of the active substances in the coating may be carried out in a thermal homogenizer such as, for example, thermal mixers, thermal kneading apparatus, roll mills or screw systems. The active substance may be added to the completely prepared coating, or equally well may be incorporated into an intermediate stage or into the initial mixture.

The stocking materials may comprise at least one interlooped elastic filament and/or at least one interwoven elastic filament.

Stocking materials of this kind are used to produce stockings which generally comprise a spatially limited tubular knitted material. Circularly loop-drawn and loop-formed tubes of elastic material, especially fibres or filaments, are advantageous. Natural- and synthetic-based starting materials are used as the basis, for instance polyesters, polyester amides, polyurethanes, polyolefins, polyacrylates, polyvinyl compounds and block copolymers, such as styrene block copolymers, and also native or regenerated cellulose.

On the basis of the selection of the materials, their confection and further processing, a wide field of product possibilities is covered. Anatomical shaping and design in accordance with the desired fields of use and indications is possible.

The stocking with the antislip coating should exert a compressive pressure of from 8 to 25 mm Hg in particular at an extension of from 10% to 350%.

The stocking should have a pressure characteristic which decreases from the distal to the proximal.

The relative decrease in the compressive pressure should be not more than 80%, preferably from 30% to 70%. The stocking preferably has a length of less than 130 cm. Preference is given to stockings having a length of from 30 to 110 cm, with particular preference from 35 to 95 cm. The extent of the product in the extended state is up to 95 cm, preferably less than 90 cm, with particular preference from 16 to 87 cm.

The coating of a stocking in accordance with the invention surprisingly shows that by the fixing of the composition on the inner face the rolling-up of the stocking edge is prevented. Achieved width-related flexural stiffnesses (DIN 53121) of at least 40 cN×mm, preferably from 80 to 350 cN×mm, with particular preference from 100 to 180 cN×mm, are advantageous.

In one very particular embodiment, the coating is used on an essentially anatomically shaped compression stocking, formed from at least one knitted elastic filament, the anti-slip or nonslip coating being applied in the upper opening region of the stocking. The compression stocking may develop a compressive force of from 15 to 25 mm Hg in the lower stocking region and a compressive force of from 8 to 15 mm Hg in the upper stocking region, and may have a width-related flexural stiffness (DIN 53121) of from 40 cN×mm to 180 cN×mm and a pressure characteristic which decreases from the proximal to the distal.

The antislip coating comprises in this case, to the extent of from 95 to 99.8% by weight, a polyadduct based on a polytetramethylene oxide diol, 1,4-butanediol and 4,4'-diphenyl-methane diisocyanate, the weight fraction formed from polytetramethylene oxide diol and 4,4'-diphenylmethane diisocyanate being greater than 78% by weight and the molar ratio of 4,4'-diphenylmethane diisocyanate to the sum of polytetramethylene oxide diol and 1,4-butanediol being between 0.96 and 1.01.

It is advantageous if stockings provided with the coating are sterile.

The antislip or nonslip coating may be applied by the direct method or by the transfer method. It is advantageous to apply it from the melt, which does away with the need to remove auxiliaries, as is the case with coating from solutions or dispersions.

The preparation of such polyadducts is known and takes place in accordance with the batch process or in continuous preparation processes. Extrusion processes or belt casting processes for production-scale batches may be mentioned by way of example. The preparation may be carried out in one or in two or more steps.

For one particular application, the composition is applied in stripes of less than 2 mm to the edge of the stocking. In another application, small flashes or S and Z lines are attached on the stocking. The use of V stripes likewise gives advantages for specific application. In general, the extensibility depends, for one type of substance, on the degree of surface coverage and on the design. By this means it is possible in principle to meet a large number of requirements. Furthermore, application may also be combined in different forms.

Figure 1:
FIG. 1 shows a V-shaped application.
Figure 2:
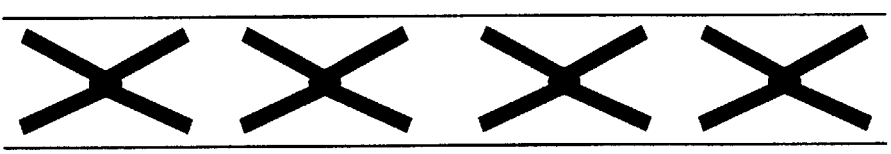
FIG. 2 shows an X-shaped application.
Figure 3:
FIG. 3 shows an application in line form.
Figure 4:
Figure 5:
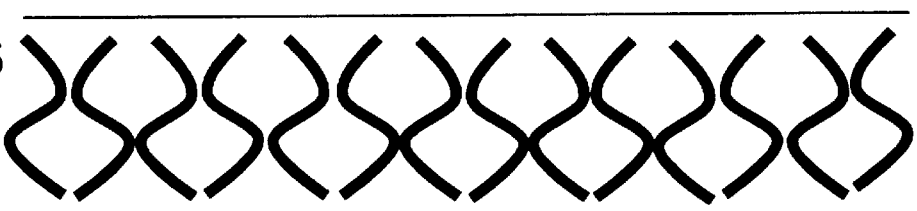

FIG. 4 likewise shows an application in line form, the lines having an inclination and being spaced more closely than in FIG. 3, and FIG. 5 represents a combination of application in S-shape and in the shape of a "2".

In the text below, preferred processes for applying the coating to the stocking are described by way of example, without wishing thereby to restrict the invention unnecessarily.

EXAMPLES

The polyadducts may be prepared without great process complexity by the "one-shot" method. It is particularly advantageous to prepare isocyanate-crosslinked oligomeric diols. It is possible to use aliphatic and aromatic isocyanates having two or three terminal functional groups.

With a view to costs and preparation, experiments based on 4,4'-diphenylmethane diisocyanate have been described by way of example. No inventive step is required by the person skilled in the art to find other experimental systems in the case where other raw materials are used.

The oligomeric polyol used (E1) was melted in a forced-air oven and brought to a starting temperature of 84° C. When this temperature was reached, the starting material (E2) and the likewise melted starting material (E3), which had been brought to a temperature of 50° C., were added. Mixing was continued until the casting temperature was reached at approximately 120° C. The reaction mixture was then cast into a Teflon-coated tub and held at 120° C. on a hotplate until the tenth minute following the commencement of reaction. The mixing temperature depends on the proportion of hard segment. Thermal conditioning took place at 85° C. for a period of 16 hours in the forced-air oven. After milling, the resultant granules were conditioned at 110° C. for a further 5 hours. In order to shorten the thermal conditioning procedure, the polyadduct may also be prepared in an extruder and granulated.

For the wash stability of the polyadduct it is important to avoid side-reactions on the side-chain, since this chain is sensitive to hydrolysis. For the reactions with isocyanates, therefore, a low allophanate group fraction in the otherwise substantially linear polymer should be achieved. The allophanate group fraction should be not more than 5% by weight. Preference is given to allophanate group fractions of less than 2% by weight, with particular preference less than 0.5% by weight. The reactive group fraction of the starting material E3 after the end of crosslinking should in total be less than 0.5%, preferably less than 0.3%.

Formulations of experiment series I

| Raw materials | Amount weighed in initially | | | | |
|---|---|---|---|---|---|
| | A | B | C | D | E |
| Polyether 1 | 129.32 | 128.57 | | | |
| Polyether 2 | | | | 134.61 | |
| Polyether 3 | | | 162.72 | | 144.47 |
| MDI | 60.09 | 60.84 | 31.63 | 53.85 | 45.03 |
| 1,4-Butanediol | 10.59 | 10.59 | 5.64 | 11.54 | 10.50 |
| Reference mass | 200 | 200 | 200 | 200 | 200 |

Formulations of experiment series II

| Raw materials | Amount weighed in initially | | |
|---|---|---|---|
| | F | G | H |
| Polyether 4 | 135.9 | | |
| Polyester 1 | | 129 | 143.61 |
| MDI | 54.24 | 60.5 | 51.06 |
| 1,4-Butanediol | | 10.5 | 5.32 |
| 1,6-Hexanediol | 9.86 | | |
| Reference mass | 200 | 200 | 200 |

The water content in the oligomeric diol (E1) and in the starting material (E2) was less than 0.3%. Hydroxyl number of the oligomeric polyols is described in the table below.

| | Diol Polyether 1 | Polyether 2 | Polyether 3 | Polyether 4 | Polyester 1 |
|---|---|---|---|---|---|
| Hydroxyl number | 112.9 | 73 | 46.3 | 112 | 115 |

For the coating of the invention it is necessary to apply the antislip substance to the stocking material. This application can take place directly or by transfer. Coating may be carried out with or without interruption. In principle, coating-free areas or else only partially coated areas may be produced. This is possible by way of the customary coating techniques such as spraying and printing, especially halftone printing, gravure printing and screen printing. A further possibility is the punching, milling or cutting of a full-area coating with the subsequent transfer of the antislip or nonslip substance.

Example 1

An anatomically shaped stocking with a compressive force of 12 mm Hg at the upper opening was produced by interlooping nylon filaments. Coating in the region of the opening took place at a temperature of 165° C. Eight stripes of 6 mm×30 mm, in V-shape, were applied. The amount of composition applied was calculated to one square metre and was 500 g/m².

The antislip substance used was a crosslinked oligomeric diol based on polyether. Further starting materials used were 1,4-butanediol and 4,4'-diphenylmethane diiso-cyanate. The hydroxyl number of the oligomeric diol was 73 mg KOH/g. The water content of the 1,4-butanediol and of the oligomeric diol was determined by the Karl-Fischer method. The water content was less than 0.2%.

The oligomeric polyol used (E1) was melted in a forced-air oven and brought to a starting temperature of 84° C. When this temperature was reached, the starting material (E2) and the likewise melted starting material (E3), which had been brought to a temperature of 50° C., were added. Mixing was continued until the casting temperature was reached at approximately 120° C. The reaction mixture was then cast into a Teflon-coated tub and held at 120° C. on a hotplate until the tenth minute following the commencement of reaction. The mixing temperature depends on the proportion of phase 1. Thermal conditioning took place at 85° C. for a period of 16 hours in the forced-air oven. After milling, the resultant granules were conditioned at 110° C. for a further 5 hours.

| Raw materials | Amount weighed in initially D |
|---|---|
| Polyether 1 | |
| Polyether 2 | 134.61 |
| Polyether 3 | |
| MDI | 53.85 |
| 1,4-Butanediol | 11.54 |
| Reference mass | 200 |

The residual isocyanate content was less than 0.1%. The first phase had a weight fraction of 78% by weight and the molar ratio of E3 to E1+E2 was 0.998.

The antislip polyadduct applied is very conforming. After ten wash cycles at 95° C., it showed a virtually unchanged antislip effect. No detachment or dissolution of the coating was found following the wash cycles. The antislip coating is silicone free and non-tacky. The flexural stiffness was 45 cN×mm.

What is claimed is:

1. Stocking having an upper opening, wherein said upper opening has an edge region, and a seamlessly attached antislip coating in the edge region of the upper opening of the stocking, the edge of the stocking producing a compressive pressure of from 3 to 45 mm Hg at an extension of from 10% to 350% and having a width-based flexural stiffness of at least 20 cN×mm under DIN 53121 testing standards, and in the region of the stocking opening, the bond strength of the coating to the stocking being at least 3 N/cm
   wherein the coating comprises a polyadduct having a phase 1 and a phase 2, the mass fraction of phase 1 being greater than 60% by weight, and wherein
   phase 1 is a polyadduct of at least one starting material E1 and at least one starting material E3, starting material E1 comprising an oligomeric diol which has a hydroxyl number of more than 20 mg KOH/g (diol) and starting material E3 comprising a silicone-free, at least bifunctional reactive starting material having a molecular weight of less than 300 g/mol, and
   phase 2 is a polyadduct comprising at least one starting material E2 and at least one starting material E3, the starting material E2 having, at least in part, terminal functional groups, and
   the coating features a molar ratio between the starting materials E3 to be crosslinked and the sum of one or more oligomeric diols (starting material E1) and the fraction of further starting materials E2 of from 0.9 to 1.1.

2. Stocking according to claim 1, comprising at least one interlooped elastic filament, at least one interwoven elastic filament or a combination thereof.

3. Stocking according to claim 1, wherein the coating is stable to hydrolysis within a temperature range from 5° C. to 100° C.

4. Stocking according to claim 1, wherein the coating has a degree of foaming of at least 5% by volume.

5. Stocking according to claim 1, wherein the coating comprises less than 5% by weight of allophonate groups.

6. Stocking according to claim 1, wherein the coating is applied to the stocking edge in the form of rods, lines, in V-form, in S-form, in Z-form or in combinations thereof.

7. Stocking according to claim 1, wherein the ratio of starting material E3 to the sum of starting materials E1 and starting materials E2 is between 0.91 and 1.05.

8. Stocking according to claim 7, wherein the weight fraction of phase 1 is at least 72%.

9. Stocking according to claim 1, wherein the oligomeric diol is a polyether diol having a hydroxyl number of from 40 to 230 mg KOH/g.

10. Stocking according to claim 1, wherein the starting material E2 is selected from the group consisting of 1,2-ethanediol, 1,4-butanediol, 1,6-hexanediol, and mixtures thereof.

11. Stocking according to claim 1, wherein the starting material E3 is an aliphatic or aromatic diisocyanate.

12. Stocking according to claim 1, wherein said stocking exerts a compressive pressure of from 8 to 25 mm Hg at an extension of from 10% to 350%.

13. Stocking according to claim 1, wherein said stocking has a pressure characteristic which decreases from the distal to the proximal.

14. Stocking according to claim 1, wherein the edge of the stocking has a width-based flexural stiffness of at least 40 cN×mm under DIN 53121 testing standards.

15. Stocking according to claim 1 formed from at least one knitted elastic filament, having an antislip or nonslip coating in the upper opening region of the stocking, having a compressive force of from 15 to 25 mm Hg in the lower stocking region and a compressive force of from 8 to 15 mm Hg in the upper stocking region, a width-related flexural stiffness of from 40 cN×mm to 180 cN×mm under DIN 53121 testing standards and a pressure characteristic which decreases from the proximal to the distal, wherein the antislip coating comprises, to the extent of from 95 to 99.8% by weight, a polyadduct based on a polytetramethylene oxide diol, 1,4-butanediol and 4,4'-diphenylmethane diisocyanate, the weight fraction formed from polytetramethylene oxide diol and 4,4'-diphenylmethane diisocyanate being greater than 78% by weight and the molar ratio of 4,4'-diphenylmethane diisocyanate to the sum of polytetramethylene oxide diol and 1,4-butanediol being between 0.96 and 1.01.

16. The stocking according to claim 4, wherein the coating has a degree of foaming from 5 to 85% by volume.

17. The stocking according to claim 16, wherein the coating has a degree of foaming from 10 to 75% by volume.

18. The stocking according to claim 17, wherein the coating has a degree of foaming from 20 to 60% by volume.

19. The stocking of claim 5, wherein the coating comprises from 0.01 to 2% by weight of allophanate groups.

20. The stocking of claim 7, wherein the ratio of starting material(s) E3 to the sum of starting materials(s) E1 and starting material(s) E2 is between 0.92 and 1.02.

21. The stocking of claim 8, wherein the weight fraction of phase 1 is from 75 to 98%.

22. The stocking of claim 21, wherein the weight fraction of phase 1 is from 76 to 95%.

23. The stocking according to claim 9, wherein the oligomeric diol is a polyether diol having a hydroxy number of from 65 to 224 mg KOH/g.

24. The stocking according to claim 23, wherein the oligomeric diol is a polyether diol having a hydroxyl number of from 70 to 150 mg KOH/g.

25. The stocking according to claim 9, wherein the oligomerig diol is a polyether diol selected from the group consisting of polytetramethylene oxide diol, polyethylene oxide diol and mixtures thereof.

26. Stocking according to claim 14, wherein the edge of the stocking has a width-based flexural stiffness (DIN 53121) of between 100 to 180 cN×mm.

* * * * *